United States Patent
Takahashi et al.

(10) Patent No.: US 7,973,202 B2
(45) Date of Patent: Jul. 5, 2011

(54) METHOD FOR PRODUCING FLUORINE-CONTAINING OLEFIN

(75) Inventors: Kazuhiro Takahashi, Osaka (JP); Masatoshi Nose, Osaka (JP); Takehiro Chaki, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/743,939

(22) PCT Filed: Nov. 11, 2008

(86) PCT No.: PCT/JP2008/070467
§ 371 (c)(1),
(2), (4) Date: May 20, 2010

(87) PCT Pub. No.: WO2009/066580
PCT Pub. Date: May 28, 2009

(65) Prior Publication Data
US 2010/0249469 A1 Sep. 30, 2010

(30) Foreign Application Priority Data
Nov. 21, 2007 (JP) .................................. 2007-301542

(51) Int. Cl.
*C07C 17/00* (2006.01)
(52) U.S. Cl. ...................................................... 570/156
(58) Field of Classification Search .................. 570/156
See application file for complete search history.

(56) References Cited

U.S. PATENT DOCUMENTS

| | | | |
|---|---|---|---|
| 5,679,875 A | 10/1997 | Aoyama et al. | |
| 5,849,658 A | 12/1998 | Shibanuma et al. | |
| 6,455,745 B1 | 9/2002 | Takahashi et al. | |
| 2007/0100175 A1 | 5/2007 | Miller et al. | |
| 2007/0179324 A1 | 8/2007 | Van Der Puy et al. | |
| 2007/0238908 A1* | 10/2007 | Merkel et al. | 570/136 |

FOREIGN PATENT DOCUMENTS

| | | |
|---|---|---|
| EP | 0 974 571 A2 | 1/2000 |
| JP | 2000-34237 A | 2/2000 |
| JP | 3158440 B2 | 4/2001 |
| JP | 3412165 B2 | 6/2003 |
| WO | WO 93/25510 A1 | 12/1993 |
| WO | WO 2007/056194 A1 | 5/2007 |

* cited by examiner

*Primary Examiner* — Jafar Parsa
(74) *Attorney, Agent, or Firm* — Birch, Stewart, Kolasch & Birch, LLP

(57) ABSTRACT

The present invention aims to reduce an amount of by-products generated in a reaction step for obtaining fluorine-containing olefin, and thereby to obtain fluorine-containing olefin as a target substance with a higher selectivity than that in the conventional method.
In a reaction step for generating fluorine-containing olefin by a dehydrohalogenation reaction from fluorine-containing halogenated propane expressed by a general formula $CF_3CH_{(2-n)}X_nCH_{(3-m)}X_m$ (wherein n=0, 1 or 2; m=1, 2 or 3; and n+m≦3; and X is selected from F, Cl and Br, independently), fluorochromium oxide having a fluorine content not less than 30% by weight is used as a catalyst.

6 Claims, No Drawings

METHOD FOR PRODUCING FLUORINE-CONTAINING OLEFIN

TECHNICAL FIELD

The present invention relates to a method for producing fluorine-containing olefin, and more specifically a method for producing fluorine-containing olefin comprising a reaction step wherein fluorine-containing olefin is generated by a dehydrohalogenation reaction from fluorine-containing halogenated propane.

BACKGROUND ART

Previously, CFCs (chlorofluorocarbons) and HCFCs (hydrochlorofluorocarbons) were used as a refrigerant substance, but they may destroy an ozone layer. Then, HFCs (hydrofluorocarbons), more specifically HFC-125 (pentafluoroethane), HFC-32 (difluoromethane) and the like become to be used as an alternate refrigerant substance, widely. However, HFC-125 and HFC-32 have a strong potential for heat-trapping, so that there is concern that the diffusion thereof may affect global warming. Although they are recovered from disposed apparatuses to prevent diffusion and thus global warming, it is impossible to recover all of them. Also, diffusion by leakage can not be disregarded. Use of $CO_2$ or hydrocarbon-based compounds as another alternate refrigerant substance is considered, but they have many problems in its efficiency and safety.

Recently, as an alternate refrigerant substance which is able to solve such problems, 1,1,1,2,3-pentafluoropropene ($CF_3CF=CHF$, hereinafter also referred to as "HFC-1225ye") and 1,1,1,2-tetrafluoropropene ($CF_3CF=CH_2$, hereinafter also referred to as "HFC-1234yf") come to the front, both of which are HFCs of olefins having a low global warming potential.

These fluorine-containing olefins can be produced by a dehydrohalogenation reaction of corresponding fluorine-containing halogenated alkanes (see, for example, Patent Citations 1-3).

Patent Citation 1: JP 3158440 B2
Patent Citation 2: US 2007/0179324 A1
Patent Citation 3: WO 2007/056194 A1
Patent Citation 4: JP 3412165 B2
Patent Citation 5: JP 2000-34237 A

DISCLOSURE OF INVENTION

Technical Problem

However, the conventional method for producing fluorine-containing olefin has a drawback of generating a large amount of by-products. Especially in the reaction generating HFC-1225ye by a dehydrohalogenation reaction from 1,1,1,2,3,3-hexafluoropropane (HFC-236ea), by-products of HFC-23 (trifluoromethane), HFC-143a (1,1,1-trifluoroethane), HFC-134 (1,1,2,2-tetrafluoroethane) and the like generate, which are low boiling components. These by-products also have a strong potential for heat-trapping, there is concern that the emission thereof to the air may affect global warming. Especially, HFC-134 has a boiling point near that of HFC-1225ye as a target substance (−19.7° C. for HFC-134; −19.5° C. for (Z)-HFC-1225ye; −15.3° C. for (E)-HFC-1225ye; each of which is a normal boiling point under the pressure of 0.1013 MPa (1 atm)), and therefore it can not be readily removed by distillation. Further, when these by-products generate, an yield decreases, so that they will cause an increase in the cost.

The present invention aims to provide a method for producing fluorine-containing olefin, which method can reduce an amount of by-products generated in a reaction step for obtaining fluorine-containing olefin, and thereby can obtain fluorine-containing olefin as a target substance with a higher selectivity than that in the conventional method.

Technical Solution

In one aspect of the present invention, there is provided a method for producing fluorine-containing olefin, comprising a reaction step wherein fluorine-containing olefin is generated by a dehydrohalogenation reaction from fluorine-containing halogenated propane expressed by a following general formula:

$$CF_3CH_{(2-n)}X_nCH_{(3-m)}X_m \qquad (I)$$

wherein n=0, 1 or 2; m=0, 1, 2 or 3; and n+m≦3; and X is selected from F, Cl and Br, independently, characterized in that fluorochromium oxide having a fluorine content not less than 30% by weight is used as a catalyst in the reaction step.

According to the present invention, since fluorochromium oxide having a fluorine content not less than 30% by weight (hereinafter also referred to as a "highly-fluorinated fluorochromium oxide catalyst") is used as a catalyst for the dehydrohalogenation reaction, an amount of by-products can be reduced effectively, and fluorine-containing olefin as a target substance can be obtained with a higher selectivity than that in the conventional method.

The highly-fluorinated fluorochromium oxide catalyst itself may be used in a reaction for fluorinating tetrachloroethylene or the like with hydrogen fluoride (see, for example, Patent Citation 4). However, the present invention utilizes a dehydrohalogenation reaction from fluorine-containing halogenated propane which is totally different from the fluorinating reaction with hydrogen fluoride. In addition, a highly-active catalyst promotes generally not only an intended reaction for generating a target substance, but also a side reaction(s) for generating by-products, and therefore a more amount of by-products generated will be expected.

Contrary to the above, the present inventors have found uniquely that when a highly-fluorinated fluorochromium oxide catalyst is used in the reaction step wherein fluorine-containing olefin is generated by a dehydrohalogenation reaction from fluorine-containing halogenated propane expressed by the above general formula (I), it becomes possible to effectively reduce an amount of by-products and obtain fluorine-containing olefin as a target substance with a higher selectivity than that in the conventional method, while the activity of catalyst is retained at a high level, and thereby the present invention has been accomplished. The use of a highly-fluorinated fluorochromium oxide catalyst brings about significant effects, compared with the case using a fluorochromium oxide catalyst having a less fluorine content (hereinafter also referred to as a "slightly-fluorinated fluorochromium oxide catalyst").

For the present invention, X in the above general formula (I) is selected from F, Cl and Br, independently, and X is preferably F.

The fluorine content of the highly-fluorinated fluorochromium oxide catalyst used for the present invention is not less than 30% by weight, preferably it is not less than 30% by weight and not larger than about 45% by weight. The fluorine content of 30-45% by weight can reduce an amount of by-products more effectively, and further improve a selectivity of fluorine-containing olefin as a target substance.

In one mode of the present invention, fluorine-containing halogenated propane is 1,1,1,2,3,3-hexafluoropropane (HFC-236ea), and fluorine-containing olefin generated by the dehydrohalogenation (more specifically, HF elimination) reaction is 1,1,1,2,3-pentafluoropropene (HFC-1225ye). Thus, according to this mode, there is provided the method for producing HFC-1225ye.

In another mode of the present invention, fluorine-containing halogenated propane is 1,1,1,2,2-pentafluoropropane (HFC-245cb), and fluorine-containing olefin generated by the dehydrohalogenation (more specifically, HF elimination) reaction is 1,1,1,2-tetrafluoropropene (HFC-1234yf). Thus, according to this mode, there is provided the method for producing HFC-1234yf.

Advantageous Effects

According to the present invention, since fluorochromium oxide having a fluorine content not less than 30% by weight is used as a catalyst for the HF elimination reaction, an amount of by-products can be reduced effectively, and fluorine-containing olefin as a target substance can be obtained with a higher selectivity than that in the conventional method.

BEST MODE FOR CARRYING OUT THE INVENTION

Embodiment 1

At first, a highly-fluorinated fluorochromium oxide catalyst is prepared. Fluorochromium oxide can be obtained by fluorinating chromium oxide with HF (see, for example, Patent Citations 4 and 5). Highly-fluorinated fluorochromium oxide can be obtained by fluorinating chromium oxide with HF at a higher temperature for a longer time than normal, and also obtained by using fluorochromium oxide for fluorinating halogenated alkyl with HF (see Patent Citation 5).

The highly-fluorinated fluorochromium oxide catalyst has a fluorine content not less than 30% by weight, and preferably has a fluorine content of 30-45% by weight. The fluorine content can be measured from a change in weight of the catalyst or a general quantitative analysis method for chromium oxide. A specific surface area of the highly-fluorinated fluorochromium oxide catalyst (by the BET method) is usually 25-130 $m^2/g$, and preferably 40-100 $m^2/g$, but not limited thereto.

Also, fluorine-containing halogenated propane is prepared to be used as a raw material. Fluorine-containing halogenated propane is expressed by a following general formula:

$$CF_3CHXCHX_2 \quad (I')$$

wherein X is selected from H and F, independently. For example, it may be 1,1,1,2,3,3-hexafluoropropane (HFC-236ea) or 1,1,1,2,2-pentafluoropropane (HFC-245cb), but not limited thereto.

Then in a reaction step, fluorine-containing halogenated propane is contacted in a gas state with the highly-fluorinated fluorochromium oxide catalyst described in the above. A contacting form is not specifically limited, but it may be of, for example, a fixed-bed type or a fluidized-bed type.

The reaction conditions are variable depending on the used catalyst and raw material and so on. For example in a case under a normal pressure, a temperature of about 200-600° C., preferably about 250-450° C. and a contact time of about 0.1-300 seconds, preferably about 0.5-120 seconds may be applied.

In this reaction step, HF is eliminated from fluorine-containing halogenated propane to generate fluorine-containing olefin. Fluorine-containing olefin as a target substance is 1,1,1,2,3-pentafluoropropene (HFC-1225ye) in the case using HFC-236ea as fluorine-containing halogenated propane of a raw material, and is 1,1,1,2-tetrafluoropropene (HFC-1234yf) in the case using HFC-245cb, but not limited thereto. It is noted that HFC-1225ye has two isomers of (Z)-1,1,1,2,3-pentafluoropropene and (E)-1,1,1,2,3-pentafluoropropene (hereinafter also referred to as "(Z)-HFC-1225ye" and "(E)-HFC-1225ye", respectively). A selectivity of HFC-1225ye means the sum of these isomers.

As described in the above, fluorine-containing olefin can be produced. According to this embodiment, since the highly-fluorinated fluorochromium oxide catalyst is used as a catalyst for the HF elimination reaction, an amount of by-products can be reduced effectively, and fluorine-containing olefin as a target substance can be obtained with a higher selectivity than that in the conventional method.

EXAMPLES

Hereinafter, the present invention will be further explained through examples of the present invention and comparative examples.

Example 1

HF Elimination Reaction from HFC-236ea

At first, chromium oxide as a precursor of a catalyst was prepared with reference to the method described in Patent Citation 4. An amount of 10% ammonia water was added to 765 g of 5.7% aqueous solution of chromium nitrate, and thereby generated precipitate was collected by filtration, washed and then dried in air at 120° C. for 12 hours to give chromium hydroxide. This chromium hydroxide was molded into pellets of 3.0 mm in diameter and 3.0 mm in height. The pellets were calcined at 400° C. for 2 hours in a nitrogen flow to give chromium oxide. A specific surface area of the obtained chromium oxide (by the BET method) was about 200 $m^2/g$.

Next, chromium oxide obtained in the above was heated together with hydrogen fluoride while a temperature is gradually increased from 200° C. to 360° C., and after the temperature reached 360° C., it was fluorinated with HF for 220 hours to give fluorochromium oxide (see Patent Citation 5). A specific surface area of the obtained fluorochromium oxide (by the BET method) was 70 $m^2/g$, and its fluorine content was 31.4% by weight. Thus, the highly-fluorinated fluorochromium oxide catalyst was prepared.

Then, into a reaction tube made of Hastelloy which was previously filled with the highly-fluorinated fluorochromium oxide catalyst prepared in the above, HFC-236ea was fed in a gas state as a raw material of fluorine-containing halogenated propane to be subjected to an HF elimination reaction.

The reaction conditions of the HF elimination reaction were as follows: a feeding amount of fluorine-containing halogenated propane into the reaction tube F0=18 Nml/min (the symbol "N" means conversion into a normal state of 0° C. and 1 atm); an amount of catalyst filling the reaction tube W=12 g; and therefore W/F0=40 $g \cdot Nml^{-1} \cdot sec$. The reaction temperature was set at 350° C. and 400° C.

After a gas flowing out of the reaction tube was collected and washed, it was analyzed by gas chromatography using a Polapack Q column. The results are shown in Table 1.

TABLE 1

| Temperature (° C.) | Conversion ratio (%) HFC-236ea | Selectivity (%) | | | | | | |
|---|---|---|---|---|---|---|---|---|
| | | $CO_2$ | HFC-23 | HFC-143a | HFC-134 | (Z)-HFC-1225ye | (E)-HFC-1225ye | HFC-236fa |
| 350 | 82.1 | 0.8 | 0.1 | 0.4 | 0.3 | 85.0 | 12.5 | 0.9 |
| 400 | 92.0 | 1.1 | 0.1 | 0.3 | 0.4 | 82.4 | 14.3 | 1.4 |

Example 2

HF Elimination Reaction from HFC-236ea

An HF elimination reaction from HFC-236ea was conducted under the conditions same as those in Example 1, except that a highly-fluorinated fluorochromium oxide catalyst having a fluorine content of 41.2% by weight was used. The highly-fluorinated fluorochromium oxide catalyst used in this example had been obtained by using fluorochromium oxide in a fluorination reaction of HCFC-133a. The results are shown in Table 2.

TABLE 2

| Temperature (° C.) | Conversion ratio (%) HFC-236ea | Selectivity (%) | | | | | | |
|---|---|---|---|---|---|---|---|---|
| | | $CO_2$ | HFC-23 | HFC-143a | HFC-134 | (Z)-HFC-1225ye | (E)-HFC-1225ye | HFC-236fa |
| 350 | 82.1 | 0.1 | 0.0 | 0.0 | 0.0 | 86.4 | 12.7 | 0.8 |
| 400 | 92.6 | 0.2 | 0.0 | 0.0 | 0.0 | 84.0 | 14.6 | 1.2 |

Comparative Example 1

HF Elimination Reaction from HFC-236ea

An HF elimination reaction from HFC-236ea was conducted under the conditions same as those in Example 1, except that a slightly-fluorinated fluorochromium oxide catalyst having a fluorine content of 12% by weight was used. This slightly-fluorinated fluorochromium oxide catalyst had been prepared by contacting chromium oxide having a specific surface area (by the BET method) of 200 $m^2/g$ (see Patent Citation 4) with HF at 200° C. for 2 hours to fluorinate it. The results are shown in Table 3.

TABLE 3

| Temperature (° C.) | Conversion ratio (%) HFC-236ea | Selectivity (%) | | | | | | |
|---|---|---|---|---|---|---|---|---|
| | | $CO_2$ | HFC-23 | HFC-143a | HFC-134 | (Z)-HFC-1225ye | (E)-HFC-1225ye | HFC-236fa |
| 350 | 89.3 | 5.6 | 0.3 | 2.5 | 1.9 | 75.8 | 11.6 | 2.3 |
| 400 | 90.9 | 5.7 | 0.4 | 1.6 | 2.1 | 74.9 | 13.3 | 2.0 |

Comparative Example 2

HF Elimination Reaction from HFC-236ea

An HF elimination reaction from HFC-236ea was conducted under the conditions same as those in Example 1, except that the fluorinating conditions of chromium oxide in Example 1 were changed to 360° C. and 120 hours and a slightly-fluorinated fluorochromium oxide catalyst having a fluorine content of 22% by weight was used. The results are shown in Table 4.

TABLE 4

| Temperature (°C.) | Conversion ratio (%) HFC-236ea | Selectivity (%) | | | | | | |
|---|---|---|---|---|---|---|---|---|
| | | $CO_2$ | HFC-23 | HFC-143a | HFC-134 | (Z)-HFC-1225ye | (E)-HFC-1225ye | HFC-236fa |
| 350 | 85.0 | 4.7 | 0.2 | 2.1 | 1.6 | 77.9 | 11.8 | 1.7 |
| 400 | 90.9 | 5.4 | 0.3 | 1.5 | 2.0 | 75.6 | 13.4 | 1.8 |

Example 3

HF Elimination Reaction from HFC-245cb

Into a reaction tube made of Hastelloy which was previously filled with a fluorochromium oxide catalyst, HFC-245cb was fed in a gas state as a raw material of fluorine-containing halogenated propane to be subjected to an HF elimination reaction.

As the catalyst, a highly-fluorinated fluorochromium oxide having a fluorine content of 41.5% by weight was used similarly to that used in Example 2.

The reaction conditions of the HF elimination reaction were as follows: a feeding amount of fluorine-containing halogenated propane into the reaction tube F0=6 Nml/min; an amount of catalyst filling the reaction tube W=2 g; and therefore W/F0=20 g·Nml$^{-1}$·sec. The reaction temperature was set at 350° C. and 400° C.

The gas flowing out of the reaction tube was analyzed as described in Example 1. The results are shown in Table 5.

TABLE 5

| Temperature (°C.) | Conversion ratio (%) HFC-245cb | Selectivity (%) | | | | |
|---|---|---|---|---|---|---|
| | | $CO_2$ | HFC-23 | HFC-143a | HFC-1234yf | HFC-245fa |
| 350 | 60.9 | 0.1 | 0.1 | 0.0 | 99.7 | 0.1 |
| 400 | 78.4 | 0.2 | 0.1 | 0.0 | 99.6 | 0.1 |

Comparative Example 3

HF Elimination Reaction from HFC-245cb

An HF elimination reaction from HFC-245cb was conducted under the conditions same as those in Example 3, except that a slightly-fluorinated fluorochromium oxide catalyst having a fluorine content of 12% by weight was used similarly to that used in Comparative Example 1. The results are shown in Table 6.

TABLE 6

| Temperature (°C.) | Conversion ratio (%) HFC-245cb | Selectivity (%) | | | | |
|---|---|---|---|---|---|---|
| | | $CO_2$ | HFC-23 | HFC-143a | HFC-1234yf | HFC-245fa |
| 350 | 62.3 | 3.2 | 0.2 | 0.3 | 96.2 | 0.1 |
| 400 | 80.2 | 3.6 | 0.3 | 0.4 | 95.5 | 0.2 |

From the results of the examples and the comparative examples in the above, it was confirmed that as a catalyst for a reaction which generates fluorine-containing olefin from fluorine-containing halogenated propane by dehydrohalogenation (more specifically, HF elimination), the use of a highly-fluorinated fluorochromium oxide catalyst reduced an amount of by-products remarkably and gave fluorine-containing olefin as a target substance with a significantly high selectivity, compared with the case using a slightly-fluorinated fluorochromium oxide catalyst.

INDUSTRIAL APPLICABILITY

The present invention is able to produce fluorine-containing olefin such as 1,1,1,2,3-pentafluoropropene and 1,1,1,2-tetrafluoropropene, and these can be used as a refrigerant substance.

The invention claimed is:

1. A method for producing fluorine-containing olefin, comprising a reaction step wherein fluorine-containing olefin is generated by a dehydrohalogenation reaction from fluorine-containing halogenated propane expressed by a following general formula:

$$CF_3CH_{(2-n)}X_nCH_{(3-m)}X_m$$

wherein n=0, 1 or 2; m=0, 1, 2 or 3; and n+m≦3; and X is selected from F, Cl and Br, independently, characterized in that fluorochromium oxide having a fluorine content not less than 30% by weight is used as a catalyst in the reaction step.

2. The method for producing fluorine-containing olefin according to claim 1, wherein the fluorine content of said fluorochromium oxide catalyst is 30-45% by weight.

3. The method for producing fluorine-containing olefin according to claim 1, wherein fluorine-containing halogenated propane is 1,1,1,2,3,3-hexafluoropropane, and fluorine-containing olefin generated by the dehydrohalogenation reaction is 1,1,1,2,3-pentafluoropropene.

4. The method for producing fluorine-containing olefin according to claim 1, wherein fluorine-containing halogenated propane is 1,1,1,2,2-pentafluoropropane, and fluorine-containing olefin generated by the dehydrohalogenation reaction is 1,1,1,2-tetrafluoropropene.

5. The method for producing fluorine-containing olefin according to claim 2, wherein fluorine-containing halogenated propane is 1,1,1,2,3,3-hexafluoropropane, and fluorine-containing olefin generated by the dehydrohalogenation reaction is 1,1,1,2,3-pentafluoropropene.

6. The method for producing fluorine-containing olefin according to claim 2, wherein fluorine-containing halogenated propane is 1,1,1,2,2-pentafluoropropane, and fluorine-containing olefin generated by the dehydrohalogenation reaction is 1,1,1,2-tetrafluoropropene.

* * * * *